United States Patent
Unwin et al.

(10) Patent No.: US 9,316,613 B2
(45) Date of Patent: Apr. 19, 2016

(54) PIPETS CONTAINING ELECTROLYTE AND ELECTRODES

(75) Inventors: Patrick Unwin, Birdingbury (GB); Neil Ebejer, St. Julians (GB)

(73) Assignee: The University of Warwick, Coventry West Midlands (GB)

(*) Notice: Subject to any disclaimer, the term of this patent is extended or adjusted under 35 U.S.C. 154(b) by 0 days.

(21) Appl. No.: 13/816,347

(22) PCT Filed: Aug. 11, 2011

(86) PCT No.: PCT/GB2011/051518
§ 371 (c)(1),
(2), (4) Date: Feb. 11, 2013

(87) PCT Pub. No.: WO2012/020264
PCT Pub. Date: Feb. 16, 2012

(65) Prior Publication Data
US 2013/0140191 A1   Jun. 6, 2013

(30) Foreign Application Priority Data
Aug. 11, 2010 (GB) .................................. 1013436.9

(51) Int. Cl.
*G01N 27/416* (2006.01)
*B82Y 35/00* (2011.01)
*G01Q 60/60* (2010.01)

(52) U.S. Cl.
CPC .............. *G01N 27/416* (2013.01); *B82Y 35/00* (2013.01); *G01Q 60/60* (2013.01)

(58) Field of Classification Search
CPC ... G01N 27/26; G01N 27/416; G01N 27/453; G01N 35/1011; G01N 2035/1053; G01N 2035/103; G01N 2035/1048; G01N 2035/1039; G01N 33/5438; B01L 3/020279; B01L 3/021; B01L 2200/02; B01L 2300/0896; C12M 41/48; C12M 29/10; B01J 2219/00364; B01J 2219/000371; Y10S 977/852; Y10S 977/08; B82Y 35/00; B82Y 15/00; G01Q 80/00; G01Q 60/44

USPC ................ 204/450, 600; 205/790; 422/82.01, 422/68.1; 435/287.1
See application file for complete search history.

(56) References Cited

U.S. PATENT DOCUMENTS 4,924,091 A * 5/1990 Hansma et al. .................... 850/1
5,382,336 A * 1/1995 Bard et al. ................. 205/790.5
(Continued)

FOREIGN PATENT DOCUMENTS

WO    WO 2008/075842    *  6/2008

OTHER PUBLICATIONS

Rodolfa et al., Angew. Chem. Int. Ed., 2005, 6854-6859.*
(Continued)

*Primary Examiner* — Jennifer Dieterle
(74) *Attorney, Agent, or Firm* — Klein, O'Neill & Singh, LLP

(57) ABSTRACT

Apparatus comprises a pipet comprising first and second channels separated by a septum and having a tip at which each of the first and second channels is open; an electrolyte solution contained within both the first and second channels of the pipet; a first electrode extending into the electrolyte in the first channel of the pipet; a second electrode extending into the electrolyte in the second channel of the pipet; means for applying a potential difference between the first and second electrodes; means for measuring alternating current components of a current flowing to or from the first electrode; means for applying an oscillatory perturbation to the pipet; and means responsive to the alternating current measured to be flowing to or from the first electrode to adjust a position of the pipet such as to control a separation between the tip of the pipet and a surface of interest.

19 Claims, 2 Drawing Sheets

(56) References Cited

U.S. PATENT DOCUMENTS

| | | | |
|---|---|---|---|
| 6,621,079 B1* | 9/2003 | Shao et al. | 250/306 |
| 2004/0182707 A1* | 9/2004 | Jardemark et al. | 204/451 |
| 2008/0075635 A1* | 3/2008 | Wang | 422/104 |
| 2009/0205960 A1* | 8/2009 | Schaffer et al. | 204/452 |
| 2012/0225435 A1* | 9/2012 | Seger et al. | 435/7.1 |

OTHER PUBLICATIONS

Chen et al.—Annual Review of Analytical Chemistry 2012.5:207-228.*

International Preliminary Report on Patentability on related PCT application (PCT/GB2011/051518) from International Bureau of WIPO dated Feb. 21, 2013.

Ebejer et al., "Localized High Resolution Electrochemistry and Multifunctional Imaging: Scanning Electrochemical Cell Microscopy" American Chemical Society, Analytical Chemistry, vol. 82, No. 22, pp. 9141-9145, Nov. 15, 2010.

International Search Report on related PCT application (PCT/GB2011/051518) from International Searching Authority (EPO) dated Oct. 14, 2011.

Lai et al., "Visualizing Zeptomole (Electro)Catalysis at Single Nanoparticles within an Ensemble" Journal of the American Chemical Society, vol. 133, pp. 10744-10747, Jun. 14, 2011.

Spaine et al., "A Positionable Microcell for Electrochemistry and Scanning Electrochemical Microscopy in Subnanoliter Volumes" American Chemical Society, Analytical Chemistry, vol. 73, No. 5, pp. 930-938, Mar. 1, 2001.

Written Opinion on related PCT application (PCT/GB2011/051518) from International Searching Authority (EPO) dated Oct. 14, 2011.

* cited by examiner

PIPETS CONTAINING ELECTROLYTE AND ELECTRODES

CROSS-REFERENCE TO RELATED APPLICATION

This application is a national phase filing, under 35 U.S.C. §371(c), of International Application No. PCT/GB2011/051518, filed Aug. 11, 2011, the disclosure of which is incorporated herein by reference in its entirety.

FIELD OF THE INVENTION

The present invention relates to pipets containing electrolyte and electrodes. The embodiments relate to the fields of electrochemistry and functional imaging.

BACKGROUND TO THE INVENTION

Among scanned probe microscopies (SPMs), electrochemical microscopies, such as scanning electrochemical microscopy (SECM), have attracted considerable attention as a means of mapping the function, as well as topography of a wide range of surfaces and interfaces. Amperometric SECM generally employs a working electrode tip, as part of an electrochemical cell, in which an electrolyte solution bathes the entire sample of interest. While SECM has provided significant advances, there can be issues from the long exposure of the sample to solution (corrosion, passivation fouling etc.) and the SECM tip design and positioning methods presently used means that measurements of surface reactivity are made neither as directly nor precisely as desired in some instances; there are limits to the spatial resolution attainable and the type of information that can be obtained.

SUMMARY OF THE INVENTION

A first aspect of the invention provides apparatus comprising: a pipet comprising first and second channels separated by a septum and having a tip at which each of the first and second channels is open; an electrolyte solution contained within both the first and second channels of the pipet; a first electrode extending into the electrolyte in the first channel of the pipet; a second electrode extending into the electrolyte in the second channel of the pipet; means for applying a potential difference between the first and second electrodes; means for measuring alternating current components of a current flowing to or from the first electrode; means for applying an oscillatory perturbation to the pipet; and means responsive to the alternating current measured to be flowing to or from the first electrode to adjust a position of the pipet such as to control a separation between the tip of the pipet and a surface of interest.

The electrolyte solution may be an aqueous solution or other.

The apparatus may comprise means for measuring a direct current component of the current flowing to or from the first electrode.

The apparatus may comprise means for measuring a current flowing to or from a substrate on which the surface of interest is supported.

The means responsive to the alternating current detected to be flowing to or from the first electrode to adjust a position of the pipet such as to maintain a separation between the tip of the pipet and a surface of interest may be responsive to a component of the alternating current at the same frequency as a frequency of the oscillatory perturbation. Alternatively or in addition, the means responsive to the alternating current detected to be flowing to or from the first electrode to adjust a position of the pipet such as to adjust or maintain a separation between the tip of the pipet and a surface of interest may be responsive to a component of the alternating current at a harmonic of a frequency of the oscillatory perturbation. In either case, the means responsive to the alternating current detected to be flowing to or from the first electrode to adjust a position of the pipet such as to maintain a separation between the tip of the pipet and a surface of interest may be configured to adjust the height of the pipet such as to maintain a constant or substantially constant amplitude of the component of the alternating current.

The apparatus may comprise means for translating the tip of the pipet relative to the surface of interest.

The apparatus may comprise means for translating the tip of the pipet relative to the surface of interest in a unilateral linescan motion.

The apparatus may comprise user-operable means for adjusting the position of the pipet prior to operation of the means responsive to the alternating current detected to adjust the position of the pipet such as to maintain the separation between the tip of the pipet and the surface of interest.

The means for applying an oscillatory perturbation to the pipet may comprise means for applying a sinusoidal perturbation to the pipet.

The means for applying an oscillatory perturbation to the pipet may comprise means for applying a perturbation to the pipet at a frequency between 5 and 100 000 Hz.

The means for applying an oscillatory perturbation to the pipet may comprise means for applying a perturbation to the pipet at an amplitude between 1 nm and 1 μm.

The means for measuring alternating current components may be configured continuously to monitor current flowing to or from the first electrode.

The means for applying an oscillatory perturbation to the pipet may be configured to apply an oscillatory perturbation to the pipet normal or substantially normal to the surface of interest.

A second aspect of the invention provides a method comprising: providing a pipet comprising first and second channels separated by a septum and having a tip at which each of the first and second channels is open; providing an electrolyte solution within both the first and second channels of the pipet; providing a first electrode extending into the electrolyte in the first channel of the pipet; providing a second electrode extending into the electrolyte in the second channel of the pipet; applying a potential difference between the first and second electrodes; measuring alternating current components of a current flowing to or from the first electrode; applying an oscillatory perturbation to the pipet; and responding to the alternating current measured to be flowing to or from the first electrode by adjusting a position of the pipet such as to maintain a separation between the tip of the pipet and a surface of interest.

The electrolyte solution may be an aqueous solution.

The method may comprise measuring a direct current component of the current flowing to or from the first electrode.

The method may comprise measuring a current flowing to or from a substrate supporting the surface of interest.

The method may comprise responding to a component of the alternating current at the same frequency as a frequency of the oscillatory perturbation detected to be flowing to or from the first electrode by adjusting a position of the pipet such as to maintain a separation between the tip of the pipet and a surface of interest.

The method may comprise responding to a component of the alternating current at a harmonic of a frequency of the oscillatory perturbation detected to be flowing to or from the first electrode by adjusting a position of the pipet such as to maintain a separation between the tip of the pipet and a surface of interest.

The method may comprise responding to the alternating current detected to be flowing to or from the first electrode by adjusting the height of the pipet such as to maintain a constant or substantially constant amplitude of the component of the alternating current.

The method may comprise translating the tip of the pipet relative to the surface of interest.

The method may comprise translating the tip of the pipet relative to the surface of interest in a unilateral linescan motion.

The method may comprise providing user-operable means for adjusting the position of the pipet prior to responding to the alternating current detected by adjusting the position of the pipet such as to maintain the separation between the tip of the pipet and the surface of interest.

The method may comprise applying a sinusoidal perturbation to the pipet.

The method may comprise applying a perturbation to the pipet at a frequency between 5 and 100 000 Hz.

The method may comprise applying a perturbation to the pipet at an amplitude between 1 nm and 1 μm.

The method may comprise continuously monitoring current flowing to or from the first electrode.

The method may comprise providing the pipet in an air or humid environment.

A third aspect of the invention provides apparatus comprising: a pipet comprising first and second channels separated by a septum and having a tip at which each of the first and second channels is open; an electrolyte solution contained within both the first and second channels of the pipet; a first electrode extending into the electrolyte in the first channel of the pipet; a second electrode extending into the electrolyte in the second channel of the pipet; a voltage source configured to apply a potential difference between the first and second electrodes; a current meter configured to measure alternating current components of a current flowing to or from the first electrode; a mechanical oscillator configured to apply an oscillatory perturbation to the pipet; and a pipet adjustment device responsive to the alternating current detected to be flowing to or from the first electrode to adjust a position of the pipet such as to control a separation between the tip of the pipet and a surface of interest.

DETAILED DESCRIPTION

Figure 1:
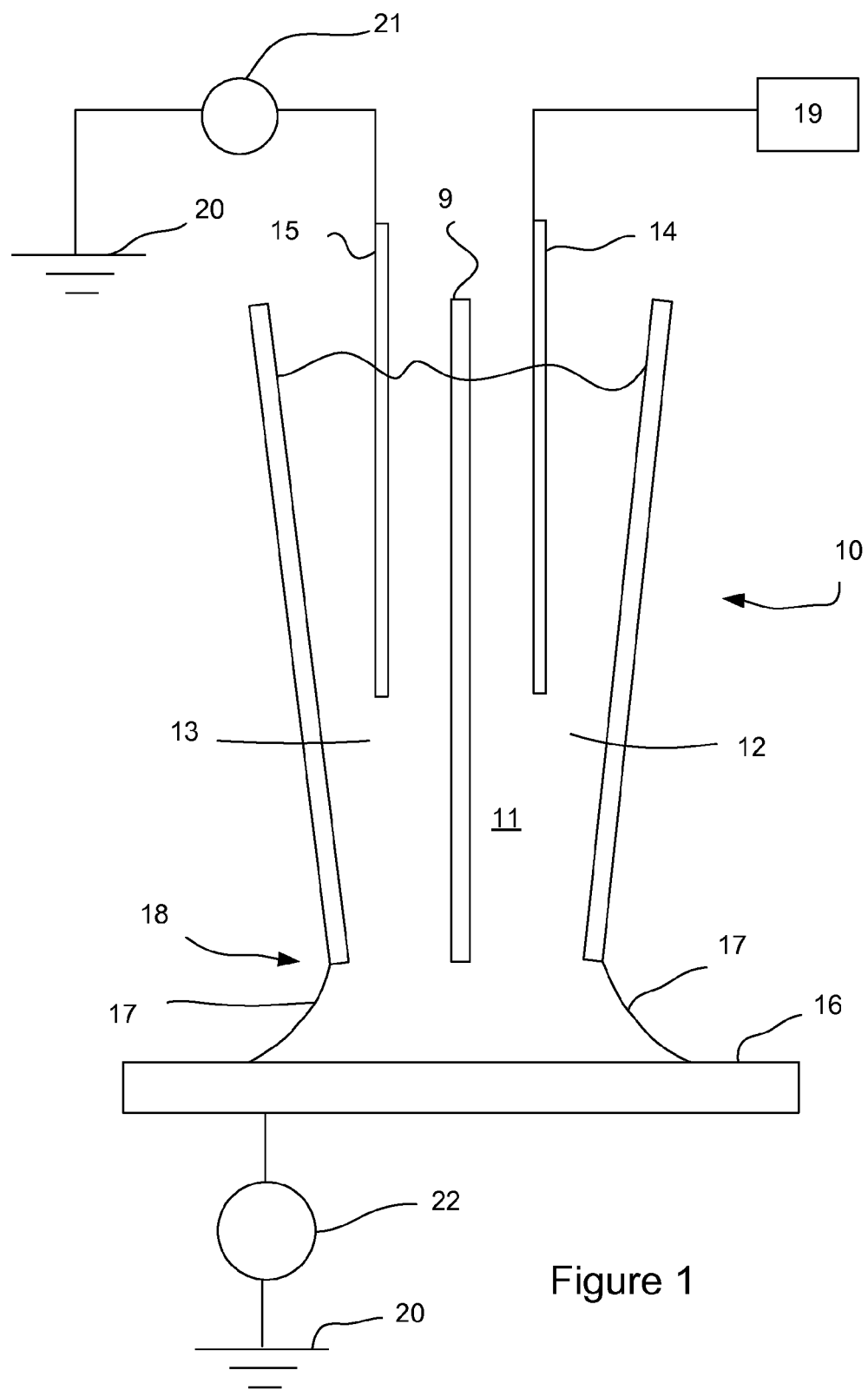
FIG. 1 shows a theta capillary, showing the meniscus coming into contact with the surface and the alternating current that arises from a periodic oscillation, as used in some exemplary embodiments of the invention

FIG. 1 shows a schematic cross section of a theta pipet 10. A localised and mobile electrochemical cell is formed using a tapered theta pipet 10. The pipet 10 has first and second channels 12, 13. The channels 12, 13 are separated by a septum 9. The pipet 10 may for instance be pulled on a laser puller such as to have the required dimensions. The pipet 10 may be of glass, quartz or similar.

The pipet 10 is provided, preferably filled, with electrolyte solution 11. The solution 11 typically is an aqueous solution but other solutions may alternatively be used. For instance, the solution may be organic or ionic. A first electrode 14 is placed in the first channel 12 of the theta pipet 10. A second electrode 15 is placed in the second channel 13. The electrodes 14, 15 may be of silver or silver chloride (Ag or AgCl), or some other type of electrode, such as some electrode commonly used in electrochemistry. The pipet 10 is placed relative to a surface of interest 16. A meniscus 17 at the lower end (tip) 18 of the pipet 10 is formed by the electrolyte 11 and extends to the surface 16 when the distance between the surface 16 and the end 18 of the pipet 10 is sufficiently small. When the distance between the surface 16 and the end 18 of the pipet 10 is not sufficiently small, the meniscus 17 forms across the end 18 of the pipet 10.

A positive potential is selectively applied by a voltage source 19 to the first electrode 14. The second electrode 15 is connected to ground potential 20 by a first ammeter 21. A second ammeter 22 is connected between the surface of interest 16 and ground potential 20. The second ammeter 22 is configured to measure surface current, denoted $i_{surf}$, although surface current is measured only if the substrate is conducting or semiconducting. The first ammeter 21 is configured to measure direct and alternating current components $i_{DC}$ and $i_{AC}$, in which the alternating component is detected via software or hardware based lockin amplifiers. The first ammeter 21 may include a high sensitivity current to voltage converter. The second ammeter 22 may also include a high sensitivity current to voltage converter.

Figure 2:
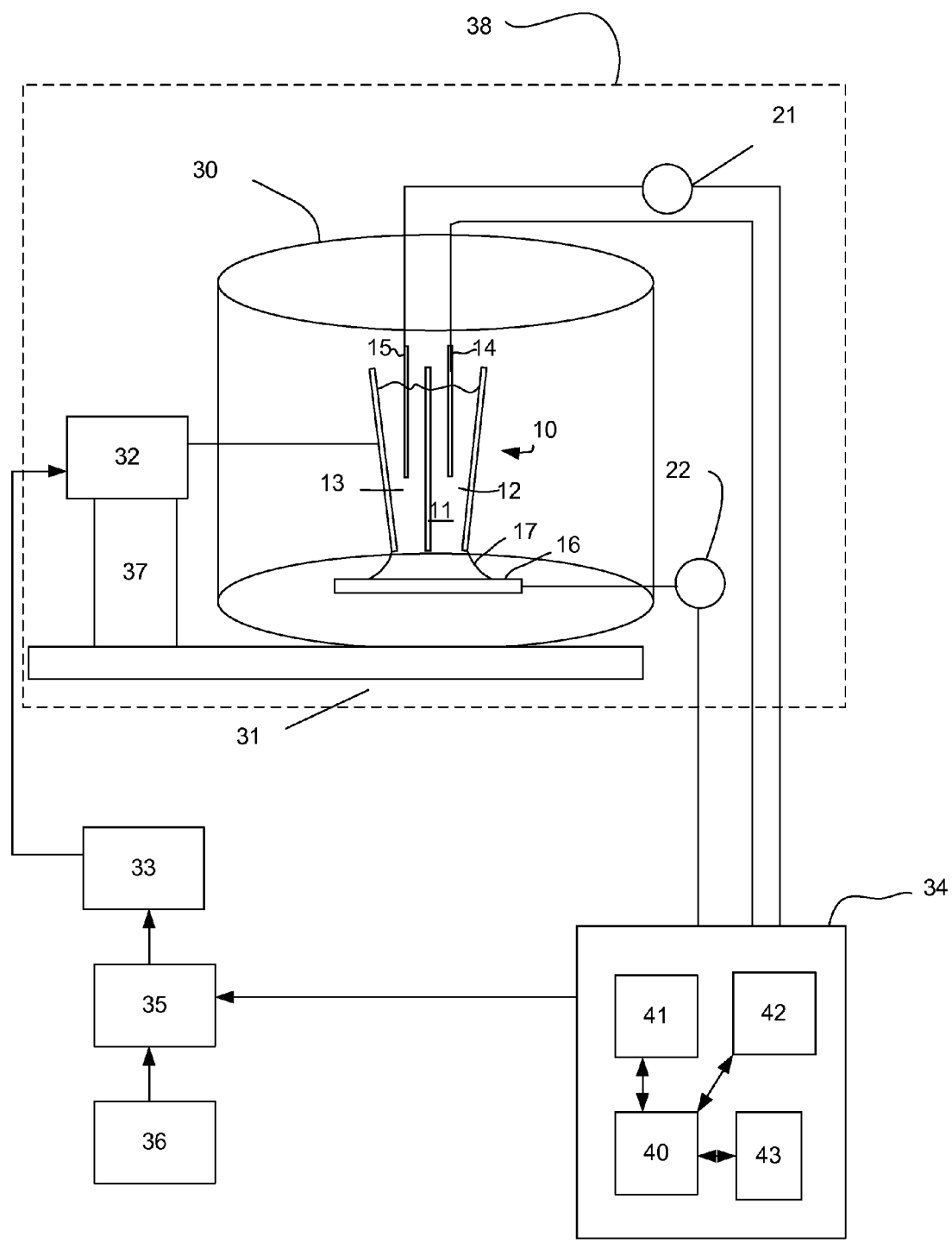
FIG. 2 shows an example configuration of an implementation of scanning electrochemical cell microscopy according to various embodiments of the invention.

An amperometric configuration is shown schematically in FIG. 2. As shown in FIG. 2, the pipet 10 is supported in a vessel or cell 30, which also contains the surface of interest 16. The vessel 30 is supported on a stable surface 31, which may for instance be an optics table with passive vibration isolation. The position of the pipet 10 with respect to the surface of interest 16 is controlled by x, y and z piezoelectric positioners 32. The positioners 32 are controlled by a piezoelectric controller 33. A controller 34, shown here in the form of a general purpose computer such as a desktop personal computer, is connected to the first and second ammeters 21, 22, to the first electrode 14 and to the positioners 32. The computer 34 is connected also to a signal adder 35, which feeds an output signal to the piezoelectric controller 33. The signal adder 35 also receives signals from a wave generator 36, which could be an external stand alone generator, or built into a hardware-based lock-in amplifier or a software based lockin amplifier, for instance. The wave generator 36 generates an oscillatory signal which is added by the signal adder 35 to a signal provided by the computer 34. The result is provided to the input of the piezoelectric controller 33, which controls the positioners 32. Positions of the piezoelectric positioners relative to the optics table 31 are controlled by x, y and z manipulator screws 37, for instance micrometer screws. The vessel 30, the bench 31, the screw 37, the positioners 32 and the ammeters 21, 22 are contained within a Faraday cage 38.

The computer 34 includes processing means 40, which may be a single core processor or have multiple cores and/or multiple processors. The computer 34 also includes volatile memory 41 and first non-volatile memory 42. The processor executes (runs) software in the form of computer programs. The programs are stored usually in the first non-volatile memory 42. The processing means 40 uses the volatile memory 41 to execute the programs. The computer 34 may be co-located with the vessel 30 or it may be remotely located. The computer 34 may be distributed. The programs may be stored in non-volatile memory that is located remotely from the processing means 40, for instance in cloud storage. The computer 34 includes second non-volatile storage 43, onto which data resulting from operation of the apparatus is recorded. The second non-volatile storage 43 may be a field programmable gate array (FPGA). The first and second non-volatile memories 42, 43 may be provided as a single memory.

In use, a potential difference applied between the two electrodes 14, 15 (which may be direct potential or alternating potential) causes a conductance current to flow between the two channels 12, 13. An oscillatory positional perturbation (oscillation amplitude), δ typically 1 nm to 1 μm at typically 5 to 100,000 Hz is applied to the pipet 10 normal to the surface of interest 16. With this oscillation, an alternating conductance current component at the frequency of the positional perturbation develops as the tip 18 encounters the surface 16. The oscillation is typically a sinusoidal oscillation of $\delta*\sin(2*\pi*f*t)$ in the height of the probe 10 about the average height of the tip 18, but other waveforms may alternatively be used.

Once the meniscus 17, at the end 18 of the pipet 10, comes into contact with the surface of interest 16, it undergoes a periodic deformation due to the perpendicular oscillation of the position of the tip 18. Using lock-in techniques, the alternating current component, $i_{AC}$, due to δ, is readily detected. A user defined value for the amplitude of the alternating current is used to land the meniscus 17 on the surface and in feedback imaging, allowing for lateral translation of the tip 18 across the surface 16, with the height of the tip 18 adjusted and measured by the piezoelectric positioner 32 or another positioning device. Localised functional and electrochemical information is then gathered by monitoring currents between the pipet channels 12, 13 and also through the surface 16 (for cases where the substrate is a conductor, semiconductor, or conducting polymer). Current followers or other current measurement instrumentation can be used for this purpose.

A detailed description of an implementation is now given with several examples. These examples are described with amperometric approach curve measurements and amperometric imaging.

Apparatus and Instrumentation

Dual channel pipet probes 10 are pulled from borosilicate theta glass capillaries (for instance of the type supplied by Harvard Apparatus, U.K.), initially of dimension) 1.5 mm (external diameter)×0.23 mm (internal diameter) with a 0.17 mm septum, using a laser puller (for instance the P-2000 supplied by Sutter Instruments, U.S.A.). For the examples herein, the end 18 of the tapered theta pipet 10 comprises of two channels 12, 13 of approximately 500 nm diameter each at the end 18 of the tip 10, although other sized orifices are possible. Typically the orifice diameter of the channels 12, 13 is in the range 10 nm to 100 μm.

The pipet 10 is mounted perpendicular to the substrate surface 16, but can instead be mounted at a different angle. Coarse control of the pulled dual channel pipet is realised manually by a three-dimensional manual x,y,z stage controlled by the manipulator screws 37. Fine control is realised by the three (x, y, z) piezoelectric positioners 32, which are fitted with strain gauge sensors (not shown). Alternatively, the piezoelectric positioners 32 may be fitted with capacitive sensors or other position-measurement devices. The x and y piezoelectric positioners 32 are operated in closed loop, whilst the z piezoelectric positioner 32 is operated in open loop. Travel dimensions of the z positioner 32 are determined from a calibration curve related to the voltage applied and are controlled by an amplifier/servo that is provided as part of the positioners 32. The piezoelectric positioner amplifier/servo is controlled by the computer 34, via the signal adder 35 and the piezoelectric controller 33. An ac signal provided by the wave generator 36 is added to the signal provided by the computer 34 the z piezoelectric positioner 32. The ac signal creates a sinusoidal oscillation of $\delta*\sin(2*\pi*f*t)$ in the height of the pipet 10 about the average height of the tip 18, but other oscillation profiles can alternatively be used.

For the case where the pipet 10 is filled with aqueous electrolyte solution 11, the vessel 30 is a humidified cell. For other examples, this is not a requirement. Many methods can be used, but one method is to use a saturated KCl (potassium chloride) solution as a moat around the sample 16 to minimise evaporation of the electrolyte 11 from the end 18 of the pipet 10.

The measured currents ($i_{DC}$ and $i_{AC}$) between the two channels 12, 13 are detected by the ammeter 21, and may be converted to a voltage before data acquisition. In the cases of the surface of interest 16 being conductive and semiconducting substrates, the second ammeter 22 is used to measure directly surface redox, charging currents, etc. This is denoted $i_{surf}$. The currents $i_{DC}$, $i_{AC}$, $i_{surf}$ and the location of the piezoelectric positioners 32 are recorded simultaneously onto the second non-volatile memory 43, to provide images of various current quantities vs tip position. The SECCM apparatus is operated in a diffusion-limited configuration, in one instance; with one of the electrodes 14, 15 in the theta pipet 10 held at a potential to electrolyse a target chemical at the surface of interest at a diffusion limited rate. Other fixed potentials can also be employed, such as the half-wave redox potential, formal potential, quarter-wave potential and three-quarter wave potential, among many other possibilities. Many other potential waveforms are possible, for example to record cyclic voltammograms, potential step, current transients, a.c. impedance measurements and other electrochemical techniques in a highly localised manner.

The use for Approach Curve measurement will now be described.

The SECCM tip 18 is moved close to the substrate surface 16 by a user operating the manipulator screws 37, observed by the user using a camera (not shown). Approach curve measurements are carried out by translating the tip 18 towards the substrate 16 using a perpendicular, z piezoelectric positioner 32. Simultaneously the tip 18 is typically oscillated at a frequency of 70 Hz (or higher up to 300 Hz or up to 1000 Hz) with a magnitude of 1-2%, or alternatively 1-20% of the inner diameter of the tip 18. This magnitude is between 10 nm and 150 nm or between 10 nm and 200 nm for typical tip diameters. The oscillation is provided by the wave generator 36. The values of $i_{AC}$ and $i_{DC}$ are measured and plotted as a function of z-piezoelectric extension. The approach curve is terminated (i.e. probe translation is halted) when an oscillatory component in the current between the capillary channels 12, 13 is detected. This oscillatory component is detected as an alternating component $i_{AC}$ by observation of the output of the first ammeter 21 through a lockin amplifier. The oscillatory component is caused by the reversible deformation of the meniscus 17 in contact with the surface 16. The probe position can also be finely controlled by gently squashing the meniscus to the desired point by approaching very precisely by use of the piezoelectric positioner 32. The value of $i_{DC}$ is measured simultaneously with $i_{AC}$ The value of $i_{DC}$ may also be observed to change at this contact point.

The use in Imaging Mode will now be described.

The tip 18 is engaged to the surface 16 using an approach curve which halts when an oscillatory component in the direct current between the pipet channels 12, 13 is detected, as described above. A suitable set-point is then chosen by monitoring the amplitude value of the resulting oscillating signal $i_{DC}$. An image is constructed typically using a series of unidirectional line scans, although other scan patterns, including those well known in the field of scanned probe microscopy, are possible. During the scan the height of the tip 18 is updated by a proportional controller, an integral controller, or other suitable controller. The proportional controller takes the form $$z_{new} = z_{old} + P^*(\text{ac amplitude}^{setpoint} - \text{ac amplitude}^{current}),$$

where $z_{new}$ and $z_{old}$ are the new and old tip height respectively, ac amplitude$^{setpoint}$ is the chosen amplitude for the ac signal before the scan and ac amplitude$^{current}$ is the ac amplitude measured at that spot.

The current between the electrodes 14, 15 in the pipet channels 12, 13, is measured during the line scans and for some substrates, a current $i_{surf}$ can also be measured directly through the substrate 16. The images of chemical activity (from the various tip current measurements) and substrate/tip height (from the location of the z piezoelectric positioner) are thus constructed simultaneously.

A number of example applications and experiments will now be described.

Example 1

The SECCM apparatus of FIGS. 1 and 2 is used to image a solid substrate 16 comprising 25 μm wide gold bands on glass. The gold bands are at 20 μm separation. The pipet probe 10 contains 20 mM KCl and a 500 mV bias is applied to the first electrode 14, with the second electrode at ground potential. Using $i_{AC}$ as a set-point, the meniscus 17 of electrolyte 11 at the end of the probe 10 maintains contact as it is scanned over the surface 16. Topographical features are thus mapped out from the changes in the z-piezoelectric positioned, recorded as a function of the x and y piezoelectric positioners 32. The data are a 2-D colour map or contour map or 3-D surface relief map, or other. These maps can be used to aid the identification of surface topography and surface features. These maps are particularly powerful when combined with the functional imaging maps described below. In the example considered, features are evident in the surface topography consistent with the gold bands of 200 nm in height.

The image recorded simultaneously is also provided as a 2-D colour map or contour map or 3-D plot, or other. These data show how $i_{DC}$ responds to the different materials that make up the substrate 16. Over the glass region, $i_{DC}$ is ca. 1.8 nA, but in the vicinity of the gold bands this value increases to 2.2 nA. This readily detected and consistent change is most likely due to a small change in the size of the meniscus 17 (wetting of the substrate).

The SECCM apparatus of FIGS. 1 and 2 also allows an $i_{AC}$ (set-point) image to be collected. This can be used to inform as to whether surface contact is maintained throughout imaging; for the example given, the set-point has a value of about 20 pA over most of the region imaged, but this error image also highlights well the leading boundary between the glass and gold, where the current attains values above the set-point and the trailing edge (with respect to x-scan direction) between the gold and glass where lower values are seen. The inventors attribute this to transient charging and discharging of the gold/electrolyte interface by the scanning probe 10 and also the response time of the feedback controller. The variation in $i_{DC}$ (and $i_{AC}$) means that the tip 10 does not strictly maintain a fixed distance from the surface 16, but provides a reasonable representation of the topography (as highlighted above). Further analysis of the $i_{AC}$ and $i_{DC}$ values can be carried out to further refine the topographical information.

This example highlights that SECCM can be used for functional imaging. Other similar applications include other surfaces 16 where there was a change in the chemical or physical character, such as a fingerprint on a metal surface, glass surface, plastic surface, paper, surface or other. In these cases, there is a change in the local wetting of the surface 16 by solution from the pipet 10 (more hydrophobic in the region of the fingerprint, for example), and this is reflected in the local value of $i_{DC}$.

Example 2

Direct amperometric imaging of electrode surfaces is demonstrated, using the SECCM apparatus of FIGS. 1 and 2 to measure the current through a substrate surface, $i_{surf}$, during the imaging process (simultaneously with and $i_{AC}$). The latter responses are essentially as already described in Example 1. The SECCM apparatus of FIGS. 1 and 2 is used to image a solid substrate comprising of 25 μm wide gold bands on glass (at 20 μm separation). The pipet probe contains 20 mM KCl and a bias is applied between the pipet channels 12, 13 (one electrode 14, 15 is at ground potential and the other is at −500 mV). Using $i_{AC}$ as a set-point, the electrolyte meniscus 17 at the end of the probe 10 maintains contact as it is scanned over the surface 16. The $i_{surf}$ response when the microband array substrate 16 is held at ground potential is measured as a function of the pipet location. When the pipet 10 is in the region of the glass 16, no current flows through the surface, because this part of the surface is an electrical insulator, but when the pipet 10 moves over the gold band a net current of 2 pA flows (average of 1000 data points measured at 25 kHz, 40 ms duration, no delay in the current measurement when moving the pipet 10 to a new location). This corresponds to a charge density of ca 15 μC cm$^{-2}$, which is of the order expected for electrodes double layer charging.

In a further example, a redox-active compound, 2 mM ferrocenylmethyl trimethylammonium (FcTMA$^+$) was introduced into the electrolyte solution 11 used to fill the pipet 10. The applied potential to the quasi-reference electrode 14 in the pipet 10, was such that FcTMA$^+$ underwent a one-electron, diffusion limited oxidation at the gold areas on the surface 16. The magnitude of the current is enhanced as a consequence. Except at the leading edge, when the pipet 10 translated from the glass area to gold and where the current is enhanced, the value measured over most of the gold band is consistent with values determined by point-by-point (of steady state) voltammetric measurements.

The experiments reported in Example 2 highlight the capability of making local electrochemical measurements of a heterogeneously active substrate surface 16. The technique highlights regions which are electrical conductors and/or capable of promoting a heterogeneous electron transfer process. A wide range of electrodes used in electroanalysis and electrocatalysis are heterogeneous by nature and SECCM is considered to be valuable for probing this heterogeneity. Furthermore, SECCM is particularly valuable for identifying corrosion sites on metal and alloys and precursor sites for corrosion pitting.

Example 3

The SECCM apparatus of FIGS. 1 and 2 can be used to image a biomineral (e.g. bone or teeth), mineral, crystal surface, tissue surface or membrane surface to investigate ion or molecule transfer between surfaces and solution. Here the surface 16 is an electrical insulator, but the composition of the electrolyte solution 11 in the pipet 10 is such that there is ion-exchange or ion transfer between the solution 11 in the pipet 10 and the surface 16 investigated. This ion-exchange or ion-transfer process occurs locally as the pipet 10 is scanned over the surface and the extent to which this occurs is reflected in the local value of $i_{DC}$ (or other current component if an oscillating potential waveform is applied to the electrode in the pipet). Consequently, the technique produces maps of local current which inform on ion exchange dynamics, such as ion uptake, ion release, dissolution, crystal growth, adsorption/desorption.

In another embodiment, which is described in "Visualizing Zeptomole (Electro) Catalysis at Single Nanoparticles within an Ensemble" by Stanley C. S. Lai, Petr V. Dudin, Julie V. Macpherson, and Patrick R. Unwin, published in J. Am. Chem. Soc. 2011, 133, 10744-10747 dated 14 Jun. 2011, an alternative arrangement is provided. Here, potentials are applied to the first and second electrodes 14, 15 separately of the potential applied to the substrate 16. As such, there is a potential difference between the electrodes 14, 15 and potential differences between each electrode and the substrate 16.

This alternative configuration has been used to measure voltammetric behaviour in localised regions of a conducting surface, biased at a variable potential (linearly scanned potential) with respect to the conductance (pipet) cell. This arrangement has also been used to carry out amperometric imaging of single walled carbon nanotube networks, grown by chemical vapour deposition, on silicon/silicon dioxide wafer, at very high resolution (tip diameter 50 nm-100 nm). The tip was scanned across the surface, in a similar manner to that described above, giving redox signals when over an electrochemically active carbon nanotube. The pattern of the nanotube networks is readily detectable also showing electrochemical activity along the entire sections of nanotubes. By monitoring the z piezo position of the pipet, quasi topography can be identified.

Importantly, this configuration allowed current maps of the surface to be recorded at a series of well-defined potentials of the surface 16, with respect to the first electrode 14.

Other common types of potential control device, such as multi-channel patch clamp amplifiers may be used to independently control the potential between electrodes 14 and 15 and the potential between 16 and 14 and to measure the resulting intrinsic currents.

In summary, SECCM allows high resolution electrochemical measurements (conductance, voltammetric-amperometric), together with topographical imaging, via a simple, moveable theta pipet containing electrolyte solution and an electrode (e.g. Ag/AgCl) in each channel; a bias is applied to one electrode, with the other at ground. Initial studies have highlighted how functional imaging of surfaces and interfaces can be implemented and one can also measure dynamic processes of surfaces such as ion uptake-release and surface electrochemistry.

There are many other uses for SECCM methodology. First, smaller pipets can be pulled in order to permit even higher resolution imaging. Second. SECCM constitutes a powerful means of probing dynamics of interfaces where there is a change in the local ion concentration; for example, ion adsorption/desorption/exchange, dissolution and growth, amongst other possibilities. The technique may also provide a means of probing electrical double layer phenomena at a variety of interfaces, as demonstrated briefly herein. Third, the ability to characterize local electrode activity is of tremendous importance, in electrocatalysis, electroanalysis and corrosion. SECCM not only provides a means of local voltammetric-amperometric analysis, but complementary information is obtained via the simultaneous conductance and topographical responses. Other well-known electrochemical techniques can be employed in conjunction with SECCM.

Additionally, SECCM as described above allows the possibility of a gas exchange at the meniscus; thus gas/liquid/solid (electrode) reactions may be investigated. It may also be possible to replace the gas phase with a variety of fluid phases, including electrolyte solutions.

Mass transport models for SECCM that permit quantitative analysis of the response have been developed. Ion fluxes and electrode surface reaction rates can already be quantified from the combined $i_{AC}$ and $i_{DC}$ responses. In future, it is envisaged to combine the $i_{AC}$ and $i_{DC}$ responses to obtain more precise topographical data.

Scanning electrochemical cell microscopy (SECCM) will now be discussed in general terms. Embodiments of SECCM utilizes a theta pipet electrochemical cell for the simultaneous measurement of the topography and a variety of local properties of interfaces, including ion uptake, charge transfer and surface wetting. Briefly, a potential is applied between two electrodes, one in each channel of a tapered glass theta pipet filled with electrolyte solution. The electrodes are held at different potentials. In practice, one electrode can be held at ground and the other is at some potential with respect to ground. The perpendicular position of the probe (normal to the surface of interest) is modulated with a small amplitude, and the direct current (d.c.) and alternating current (a.c.) responses are measured and utilized for high resolution conductance measurements and topographical imaging. When the electrolyte solution, formed at the end of the pipet, across the septum of the two channels, comes into contact with a surface, the periodic (reversible) deformation of the meniscus gives rise to an alternating current $i_{AC}$, which is not experienced when away from the surface. Thus, $i_{AC}$, can be used as a set-point to ensure the contact of the electrochemical cell with the surface. Simultaneously, the mean, or direct conductance current, $i_{DC}$ can be measured. As well as depending on the probe geometry and size, $i_{DC}$ is also sensitive to the surface properties. For example, an ion flow, from the solution in the pipet, into the surface causes a decrease of the local electrolyte concentration in the meniscus at the end of the tip, thus increasing the resistance (decreasing $i_{DC}$). Likewise, the dissolution of a salt or mineral leads to the accumulation of ions at the end of the pipet and consequently an increase in $i_{DC}$. By measuring both $i_{AC}$ and $i_{DC}$, functional imaging of interfaces can be carried out with this simple conductivity cell.

For conducting surfaces (e.g. metals, semiconductors, conducting polymers) it is possible to use the pipet as a local dynamic electrochemical (voltammetric-amperometric) cell by connecting the sample as a working electrode. Again $i_{AC}$ is used for positioning and $i_{DC}$ informs on conductance and hence the properties of the interface, but one can also measure a current through the sample due to any surface redox process, double layer charging etc. A modulated probe of the type used in embodiments of the invention has been proposed to trace the topography of surfaces (via $i_{AC}$) and to carry out local deposition of proteins, (see U.S. Pat. No. 7,297,486 B2). However, this document does not disclose DC conductance measurements and does not demonstrate that it has been recognized that $i_{DC}$ will also be very sensitive to the local environment of the probe, allowing functional imaging as we show herein. Nor has a probe of this type ever been used for direct high resolution, surface electrochemical imaging as demonstrated above. Significantly. SECCM described herein reveals that the modulated current component ($i_{AC}$) alone does not necessarily provide true topographical information.

SECCM as herein described expands the range and capabilities of pipet-based electrochemical imaging methods. The most sophisticated previous approaches have employed single channel probes and complex shear force feedback protocols or similar resonance techniques to maintain the tip in contact with the sample. A dual channel pipet-based flow cell, without any feedback control, has also been described for investigating metal dissolution which operates on much larger length scales than SECCM. SECCM uses different principles and greatly advances these confined electrochemical cells: it represents the smallest mobile electrochemical cell yet reported. It incorporates topographical mapping, as well as functional imaging coupled with direct electrochemical measurements.

SECCM is a new type of high resolution, electrochemical scanned probe microscopy technique. It allows for high resolution electrochemical measurements and imaging utilising a droplet of solution formed at the end of a theta pipet filled with electrolyte solution to allow topography and local electrochemical and surface properties to be resolved independently.

SECCM allows high spatial resolution electrochemical measurements at a wide variety of interfaces and surfaces (including electrode surfaces), and provides a means of measuring and visualizing interfacial fluxes. SECCM allows the simultaneous measurement and imaging of surface topography and interfacial properties and reactivity.

In summary, SECCM uses a glass (or quartz or similar), theta capillary 10, filled with an electrolyte solution 11 of interest. A potential difference is applied between two electrodes (often Ag/AgCl, but others can be used), one in each channel of the pipet. An alternating potential can also be applied between the channels, comprising a number of waveforms and frequencies. The application of a superimposed oscillatory component to the position of the pipet probe, normal to the surface, whilst monitoring the current between the two channels allows for tip positioning. Equivalently the sample position can be oscillated with a perpendicular motion. The oscillation leads to a component of the current that can be used as a feedback protocol to maintain an approximately constant area of the solution in contact with the surface, either for point measurements or pipet imaging. Other components of the current (e.g. mean current, first and higher harmonics) enable functional imaging of interfacial properties. Localised impedance measurements are also possible. For conducting and semiconducting surfaces, the current through the surface can also be measured.

When the liquid meniscus, formed at the end of the theta pipet, between the two channels, comes into contact with a surface, the periodic deformation of the meniscus, due to the oscillatory motion of the probe, gives rise to an alternating current component, $i_{AC}$, which is not experienced when away from the surface. Thus, $i_{AC}$, is used as a set-point to identify when the electrolyte solution makes contact with the surface. Simultaneously, the mean, or direct, current $i_{DC}$ is measured (when a fixed potential is applied) or second an alternating current at the frequency of the potential oscillation (or other frequencies) in the case of an alternating potential. The phase of the current, with respect to the potential oscillation, can also be measured. As well as depending on the probe geometry and size, is also sensitive to the surface properties, particularly the extent that the surface is wetted, and also when the surface takes up or releases ions (or molecules). When investigating conductive substrates, it is also possible to measure redox currents, charging currents, through the substrate electrode giving direct spatially resolved electrochemical currents ($i_{surf}$). In this case the sample is usually held at a fixed potential or potential waveforms well known in the field are applied and the current response recorded (steady-state, current-potential or current-time, for example).

SECCM as described herein can provide a cheap, robust and simple means to produce small-scale (moveable) electrochemical cells and a methodology that allows functional and electrochemical imaging from which substrate topography and surface activity maps can be produced. The output is often multi-coloured images or plots of region of a surface which describe the surface topography and properties, such as activity, ion uptake, wetting or other (depending on the current quantity measured). SECCM as described herein can provide a means of achieving ultra-small electrochemical cells, confined by a meniscus, formed at the end of the pipet probe. The theta pipet tips used can be fabricated using well known protocols, and can be simple and quick to prepare. The feedback (used to make contact with the surface) means that topographical information on the surface is realised. At the same time, additional information about the substrate can be obtained; for example by monitoring the direct (or mean) current between the theta pipet channels (with a fixed potential) and/or measuring the current through the surface (if a conductor or semiconductor or conducting polymer etc.).

The invention claimed is:

1. A method comprising:
   providing a pipet comprising first and second channels separated by a septum and having a tip at which each of the first and second channels is open;
   providing an electrolyte solution within both the first and second channels of the pipet;
   providing a first electrode extending into the electrolyte in the first channel of the pipet;
   providing a second electrode extending into the electrolyte in the second channel of the pipet, the second electrode at a ground potential;
   applying a potential difference between the first and second electrodes;
   applying an oscillatory perturbation to the pipet at a perturbation frequency;
   measuring alternating current components of a current flowing to or from the first electrode; and
   responding to alternating current at the perturbation frequency or at a harmonic of the perturbation frequency measured to be flowing to or from the first electrode by adjusting a position of the pipet so as to maintain a separation between the tip of the pipet and a surface of interest.

2. A method as claimed in claim 1, wherein the electrolyte solution is an aqueous solution.

3. A method as claimed in claim 1 further comprising measuring a direct current component of the current flowing to or from the first electrode.

4. A method as claimed in claim 1 further comprising measuring a current flowing to or from a substrate supporting the surface of interest.

5. A method as claimed in claim 1 wherein responding to the alternating current measured to be flowing to or from the first electrode by adjusting the position of the pipet so as to maintain the separation between the tip of the pipet and the surface of interest comprises responding to a component of the alternating current at the perturbation frequency detected to be flowing to or from the first electrode by adjusting the position of the pipet such as to maintain the separation between the tip of the pipet and the surface of interest.

6. Apparatus comprising:
- a pipet comprising first and second channels separated by a septum and having a tip at which each of the first and second channels is open;
- an electrolyte solution contained within both the first and second channels of the pipet;
- a first electrode extending into the electrolyte in the first channel of the pipet;
- a second electrode extending into the electrolyte in the second channel of the pipet, the second electrode connected to ground;
- a voltage source configured to apply a potential difference between the first and second electrodes;
- a mechanical oscillator configured to apply an oscillatory perturbation to the pipet at a perturbation frequency;
- a current meter configured to measure alternating current components of a current flowing to or from the first electrode; and
- a pipet adjustment device responsive to alternating current at the perturbation frequency or at a harmonic of the perturbation frequency detected, by the current meter, to be flowing to or from the first electrode to adjust a position of the pipet so as to control a separation between the tip of the pipet and a surface of interest.

7. Apparatus as claimed in claim 6, wherein the electrolyte solution is an aqueous solution.

8. Apparatus as claimed in claim 6, wherein the current meter is configured to measure a direct current component of the current flowing to or from the first electrode.

9. Apparatus as claimed in claim 6, wherein the current meter is configured to measure a current flowing to or from a substrate on which the surface of interest is supported.

10. Apparatus as claimed in claim 6, wherein the pipet adjustment device is responsive to the alternating current detected to be flowing to or from the first electrode to adjust a position of the pipet so as to maintain a separation between the tip of the pipet and a surface of interest is responsive to a component of the alternating current at the perturbation frequency.

11. Apparatus as claimed in claim 10, wherein the pipet adjustment device is responsive to the alternating current detected to be flowing to or from the first electrode to adjust a position of the pipet so as to maintain a separation between the tip of the pipet and a surface of interest is configured to adjust the height of the pipet so as to maintain a constant or substantially constant amplitude of the component of the alternating current.

12. Apparatus as claimed in claim 6, wherein the pipet adjustment device is responsive to the alternating current detected to be flowing to or from the first electrode to adjust a position of the pipet so as to adjust or maintain a separation between the tip of the pipet and a surface of interest is responsive to a component of the alternating current at a harmonic of the perturbation frequency.

13. Apparatus as claimed in claim 6, comprising a translator for translating the tip of the pipet relative to the surface of interest.

14. Apparatus as claimed in claim 6, comprising a translator for translating the tip of the pipet relative to the surface of interest in a unilateral linescan motion.

15. Apparatus as claimed in claim 6, comprising a user-operable position adjuster for adjusting the position of the pipet prior to operation of the pipet adjustment device to adjust the position of the pipet so as to maintain the separation between the tip of the pipet and the surface of interest.

16. Apparatus as claimed in claim 6, wherein the mechanical oscillator is configured to apply a sinusoidal perturbation to the pipet.

17. Apparatus as claimed in claim 6, wherein the mechanical oscillator is configured to apply a perturbation to the pipet at a frequency between 5 and 100 000 Hz.

18. Apparatus as claimed in claim 6, wherein the mechanical oscillator is configured to apply a perturbation to the pipet at an amplitude between 1 nm and 1 μm.

19. Apparatus as claimed in claim 6, wherein the current meter is configured continuously to monitor current flowing to or from the first electrode.

\* \* \* \* \*